United States Patent [19]

Troll

[11] Patent Number: 5,721,435
[45] Date of Patent: Feb. 24, 1998

[54] METHODS AND APPARATUS FOR MEASURING OPTICAL PROPERTIES OF BIOLOGICAL AND CHEMICAL SUBSTANCES

[75] Inventor: Mark A. Troll, Palo Alto, Calif.

[73] Assignee: Hewlett Packard Company, Palo Alto, Calif.

[21] Appl. No.: 630,054

[22] Filed: Apr. 9, 1996

[51] Int. Cl.⁶ .............................. G01N 1/28; G01N 21/00
[52] U.S. Cl. ........................ 250/559.29; 250/559.44; 356/375; 422/82.05
[58] Field of Search ........................ 250/559.29, 559.3, 250/559.4, 559.06, 559.44, 216, 237 R, 237 G; 356/320, 372, 375, 397, 398, 400, 401, 244; 435/289, 291; 422/50, 55, 82.05, 82.08

[56] References Cited

U.S. PATENT DOCUMENTS

| | | | |
|---|---|---|---|
| 4,647,531 | 3/1987 | Kamentsky | 435/7 |
| 5,083,035 | 1/1992 | Pecen et al. | 250/561 |
| 5,427,910 | 6/1995 | Kamentsky et al. | 435/6 |
| 5,532,128 | 7/1996 | Eggers et al. | 435/16 |
| 5,550,634 | 8/1996 | Nakamura | 250/559.29 |
| 5,565,988 | 10/1996 | Nara et al. | 250/559.3 |
| 5,631,170 | 5/1997 | Attridge | 436/518 |
| 5,653,939 | 8/1997 | Hollis et al. | 422/50 |
| 5,670,322 | 9/1997 | Eggers et al. | 435/6 |

OTHER PUBLICATIONS

Fodor, Stephen P.A., et al., "Light–Directed, Spatially Addressable Parallel Chemical Synthesis," *Science*, Feb. 15, 1991, pp. 767–773.

*Primary Examiner*—Edward P. Westin
*Assistant Examiner*—John R. Lee

[57] ABSTRACT

An optical measurement system includes a test surface having disposed thereon a plurality reference markings and a plurality of test spots containing chemical and biological substances. Molecules of interest contained in the chemical and biological substances are tagged with optically detectable labels. A light source generates a beam of light which is then directed by a deflecting sub-system across the test surface, thereby individually impinging the test spots and the reference markings. Optical signals resulting from the impingement are detected by a detection means, which records such detection and the time of the detection. The reference markings have optically unique signatures to distinguish the markings from the optical signatures of the signals emitted from the chemical and biological substances in the test spots. The reference markings are spaced apart at known distances and serve to provide a constant calibration of the scan speed of the beam of light. In one embodiment, a Winston concentrator directs the light emanating from the test surface to the detector. In another embodiment, an off-axis parabolic mirror arrangement directs the light to the detector.

21 Claims, 4 Drawing Sheets

METHODS AND APPARATUS FOR MEASURING OPTICAL PROPERTIES OF BIOLOGICAL AND CHEMICAL SUBSTANCES

TECHNICAL FIELD

The present invention relates generally to biological and chemical assays, and more specifically to optical detection of biological and chemical substances.

BACKGROUND ART

It is common practice in biochemical assays to measure the presence of substances such as hormones, antibodies or nucleic acids. Typically, such chemical and biological materials are subjected to experimental procedures which render them optically detectable. For example, fluorescent material may be used to tag certain molecules present in biochemical specimens so that their presence (or absence) can be determined. This is usually done by placing the specimen in one well of a multi-well plate and performing the desired experiment. Greater efficiency can be achieved by forming an array of a large number of such test spots on a plate and performing the experiments en masse.

In a typical experiment, a plate containing an array of optically labeled biochemical test spots is scanned by a laser. A scanning sub-system directs the laser beam across the surface of the plate so as to impinge upon the individual test spots formed on the plate. Optical signals resulting from impingement of the laser beam is then detected by a detector and recorded for later analysis.

Quite often, plates containing arrays of optically labeled biochemical specimens (test spots) are prepared in advance for subsequent experimentation. For example, a set of such preformed plates may be prepared by a first laboratory and sent to other laboratories for study. While it is known beforehand what biological or chemical substances are in each test spot, the precise spatial information of the test spots on a plate is lost. This is due to differences between the processing equipment used by the first laboratory to place the specimens on the plate and the equipment used by the other laboratories to perform the experiments on the specimens. There is no reliable reference to the machine which originally placed the test spots, and so it is extremely difficult to provide proper registration of the test spots in subsequent machines. Since the test spots are quite small and closely spaced, any small error in registration when setting up the plate for an experiment would result in the collection of useless data.

Another source of error is in the scanning sub-system of the laser system used during the experiments. Typically, the beam is scanned across the plate at fairly high rates. It is, therefore, difficult to precisely control the position of the beam at any given instant in time. The result is that the scan speed of the beam will vary during the course of the scan. In addition, tolerances in the scanning mechanics will vary with time due to wear, further exacerbating the problem.

It is possible, nevertheless, to ensure proper registration of the array of specimens and to ensure accurate scan rates. Highly accurate plates and highly accurate laser scanning systems can be employed. Such high precision comes with an equally high cost, both in terms of acquisition of the equipment and of the maintenance effort to keep the machine tuned and properly calibrated. While commercial laboratories, such as drug companies, and other large and highly funded research labs can afford these sophisticated machines, it is not likely that such machines will be found in a smaller operation such as a medical office.

Alternatively, a computer imaging system can be employed to form a digital image of the array of specimens. The images can then be digitally processed and analyzed to ascertain the nature of the detected optical properties and the position of each detection. However, imaging systems require high precision optics in order to produce faithful images of the imaged subject. Again, the cost of such systems typically exceeds the financial resources of a small medical practice.

What is needed is an approach whereby spatial accuracy of arrays of optically tagged biological and chemical specimens can be ascertained without the use of sophisticated and otherwise very expensive equipment. A technique is needed which allows arrays of biochemical specimens to be prepared without concern for the dimensional tolerances of the machines which prepare the plates and of the machines which later perform the experiments.

SUMMARY OF THE INVENTION

A method and system are disclosed for measuring optical signals generated by optically tagged molecules in a plurality of biological and chemical specimens. A test surface is divided into a plurality of selected areas, forming test spots onto which the specimens are placed. The test surface further includes reference markings such as grid lines or other optically identifiable markings which are interspersed among the test spots and spaced apart by known measures of separation. The reference markings have unique optical signatures in order to distinguish from the optical characteristics of the specimens.

A light source is provided for illuminating the test surface. Preferably, the light source, e.g. laser, generates a collimated beam. The collimated beam selectively illuminates the reference marks and the specimens by being scanned across the test surface with a deflection device. The resulting optical signals from each of the reference marks and the specimens is transmitted to an optical detector. A recording device, such as a computer memory, records the detected signals and the time of occurrence of the signals. The recorded signal detection times, along with the known relative positions of the reference markings, allows for an accurate determination of the positions of the specimens. In one embodiment, the reference markings have measures of separation that vary with the location of the markings on the test surface. In addition, the light source can be amplitude modulated in order to better discriminate from ambient or stray light.

In another embodiment of the present invention, an off-axis parabolic mirror is used to transmit the optical signals to the detector. A parabolic mirror is positioned between the test surface and the optical detector such that light emanating from the test surface is reflected by the mirror toward the optical detector. In yet another embodiment, a compound parabolic concentrator is used to collect the emitted light and transmit the light to the detector. The compound parabolic concentrator, also known as a Winston concentrator, is preferred over the off-axis parabolic mirror because of the greater light transmission efficiency of the former. One type of Winston concentrator employs a reflecting surface that is formed by rotating a parabolic mirror about a central axis of the concentrator, thereby allowing for the collection and transmission of light in three dimensions.

In a more generalized scheme, numerous iterations of tests and scans may be performed on the chemical and biological specimens. For example, after an initial scan, additional tests may be performed on the specimens. A subsequent scan can then be made to measure and record any optical signals resulting from the additional tests. Since the system is inherently self-calibrating, the additional scans can be performed without the need for manual alignment of the test surface.

A significant advantage of the present invention is that the light collecting and transmission optics need not be of the calibre found in typical precision imaging systems. The requirements of the optics contemplated for the present invention are simply that the optics be able to gather the light emitted from the specimens and to transmit that light to a detector. There is no need to form an accurate image of the specimens, or any image at all.

BEST MODE FOR CARRYING OUT THE INVENTION

Figure 1:
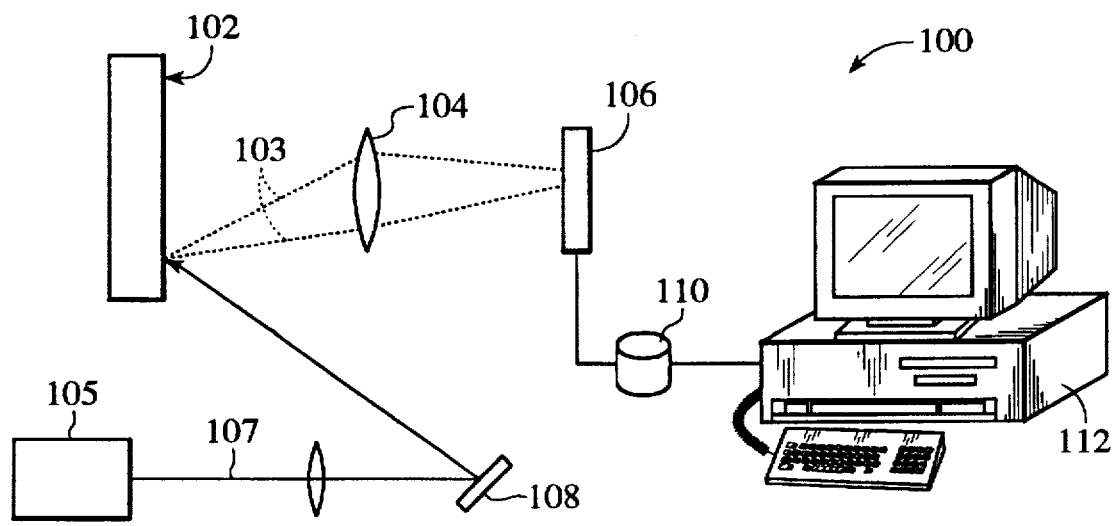
FIG. 1 is a schematic illustration of the optical measurement system of the present invention.

FIG. 1 shows in schematic form an optical measurement system 100 of the present invention. Chemical and/or biological specimens whose optical properties are of interest are disposed upon a test surface 102. A beam of light 107 is directed by a deflecting sub-system 108 to impinge areas of the test surface 102. The beam of light 107 is preferably a collimated beam as generated by a laser 105. As a result of the impinging light upon the test surface 102, optically tagged molecules in the specimens may emit optically detectable signals. The emitted light 103 resulting from the optical signals is collected by light collection optics 104 and transmitted to a detector 106. The output of the detector is stored onto a storage medium 110, along with the time of such detection. Typically, the storage medium 110 is some form of magnetic recording medium, such as a disk drive. Based upon the recorded data, the positions of the detected optical signals can be calculated by a computer 112.

Figure 2:
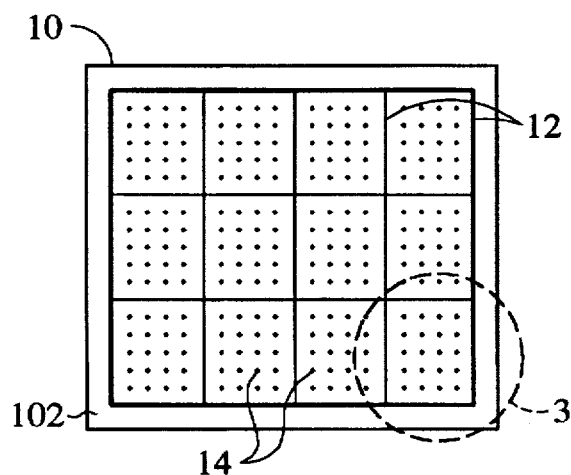
FIG. 2 illustrates a typical test surface on which chemical and biological test specimens are disposed.

Turning to FIG. 2, additional detail of the test surface 102 is provided. A face of a plate 10 serves as the test surface 102. As shown in the figure, the test surface is flat. However, this is not critical to the present invention, and as will be explained below, the test surface may in fact have an uneven contour.

The surface is divided into an array of selected areas (test spots) 14 onto which various chemical or biological substances are placed. Interspersed among the test spots 14 are reference markings 12 formed on the test surface 102. The reference markings are spaced apart by known amounts and are optically detectable. As will be explained below, the known spacings between the reference markings allows for the computation of the positions of the detected optical activity of the test spots.

Referring again to FIG. 1, the beam of light 107 is directed by the deflecting sub-system 108. Optical deflecting systems are well known in the optics arts, and any of a number of such systems can be used in the present invention. Typically, the deflecting system includes a moving mirror to which a light beam is directed and from which the light beam is reflected in a desired manner. The mirror may be a rotating prism, such as an octagonal element, or may be a galvanometer-driven mirror. Deflection of the light beam may also be accomplished by devices other than mirrors. For example, an acoustically-driven diffraction device, or other diffraction devices with variable grating parameters, can be used to effectuate controlled deflection of the light beam.

The deflecting sub-system 108 directs the light beam 107 to traverse the area of the test surface 102 in raster fashion. The deflected beam of light 107 scans the test surface 102 from top-to-bottom, one row at a time in left-to-right manner, much in the same way as an electron beam is scanned across the phosphor screen of a television set. The particular scan sequence is not crucial, however. In an alternate embodiment, for example, the light beam 107 can be made to scan the test surface 102 from left-to-right, one column at time in top-to-bottom order. In general, any known scanning technique will work equally well. Typically, the scan sequence will be dictated by the mechanics of the particular deflecting optics in use.

As the light beam 107 scans the test surface 102, optical signals will result when the light beam strikes the reference markings 12 or the chemical and biological specimens disposed in the test spots 14. The specimens have optical properties such as reflectance, fluorescence, fluorescence polarization and scattering. Optical signals in these specimens arise due to impingement of the light beam 107 during its course as it is scanned over the test surface 102. For example, fluorescence arises when light (in this case the scanning light beam 107) is absorbed by a fluorescent substance, pushing some of its electrons to a higher energy state. When those electrons return to their lower energy states, they emit a photon of light in the process; i.e. the substance fluoresces. Other substances will reflect or scatter the impinging light, rather than absorb and retransmit light. Regardless of the mechanism, however, each of the test spots 14 is likely to produce some form of optical signal when the optically tagged molecules of the specimen disposed therein are exposed to the scanning light beam 107.

Figure 3:
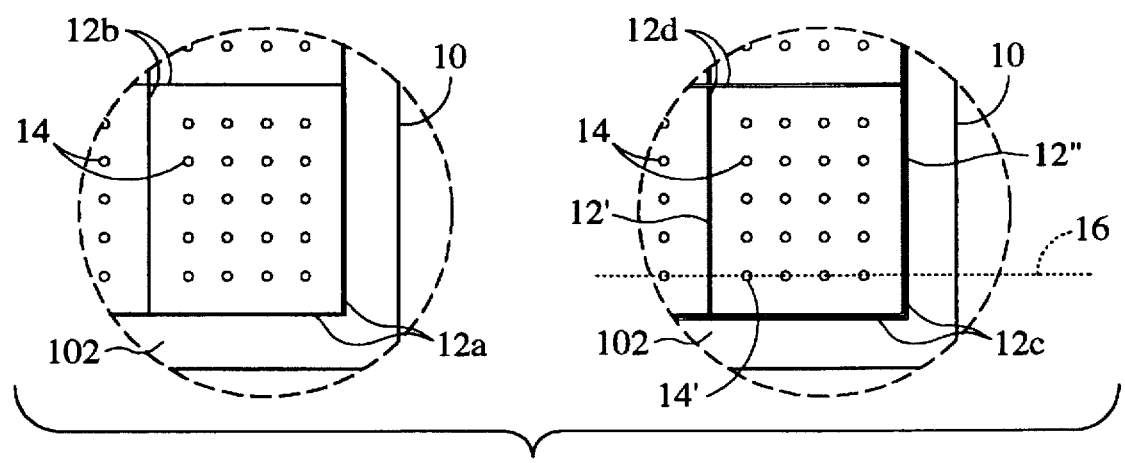
FIG. 3 shows two magnified views of the region identified in FIG. 2.

Similarly, the reference markings 12 will also produce some form of optical signal upon illumination by the light beam 107. For reasons that will become clear, it is desirable that the reference markings 12 have optical signatures that are unique to the markings in order to differentiate them from the optical signals of the specimens in the test spots 14. In the preferred embodiment, the reference markings 12 have the form of a series of grid lines as shown in FIG. 2. FIG. 3 shows magnified views of the lower right-hand corner of the plate 10, as identified in FIG. 2. In one instance, the grid lines are solid marks that have varying characteristic widths 12a, 12b. The varying widths of the solid marks 12a, 12b produce optical signatures that are unique to the grid lines when impinged upon by the light beam, and so are optically distinguishable from the specimens. Equally effective distinguishing features can be imparted to the solid marks 12a, 12b by forming the marks with highly reflective material, or fluorescent material not found in any of the specimens. Another method of distinguishing from the specimens is to form the grid lines 12 with a series of two or more closely spaced lines 12c, 12d, as shown in the other of the magnified views shown in FIG. 3. Again, such grid lines 12c, 12d have optical signatures that are distinguishable from those of the specimens.

It is noted that the specific method of uniquely identifying the grid lines is not critical. It is only required that the grid lines 12a–12d be optically distinguishable from the specimens. Moreover, the use of grid lines as reference markings is not essential to the practice of the present invention. Effective reference markings could have a form similar to that of the test spots 14, so long as the material used in such reference markings is optically unique to the markings so as to be distinguishable from the specimens.

For example, the reference markings may be formed of a layer of aluminum, or other reflective metal or alloy, using an evaporative method. Alternatively, the reference markings may be printed onto the test surface 102 with fluorescent ink. The ink may have a characteristic brightness or emit light at a particular wavelength. The reference markings may be formed so that the impinging light is reflected to a second detector (not shown) positioned specifically for the purpose of detecting the markings.

Turning back to FIG. 1, the detector 106 may be the photocathode of a photomultiplier tube, the specific type of device not being essential to the practice of the present invention. Other optical detectors are possible, such as an array of charge-coupled devices, CCDs. The use of array detectors, however, is a more costly alternative and typically requires frequent calibration. For this reason, a single detector is preferred over an array detector. In order to increase the reliability of detection, the light source 105 may include a "chopper" (not shown) positioned in the path of the light beam 107. The chopper interrupts the beam at a certain frequency, for example 40 Hz. Detection electronics in the detector 106 are synchronized with the chopper frequency to take measurements at a corresponding rate. By so doing, the detector 106 is active only during those times when the light beam 107 is present. This minimizes the detection of ambient or otherwise stray light, which is a source of noise, and so tends to increase the signal-to-noise ratio of the detection system. Alternatively, the chopper may operate with the light source 105 by modulating the amplitude of light beam in a time-varying fashion such as a sinusoid.

Referring to FIGS. 2 and 3, recall that the reference markings 12 are spaced apart by known amounts. When the light beam is scanned across the surface, the optical signals arising from impingement of the laser upon the reference markings, e.g. scattering, are detected and recorded along with the time of detection. Since the reference markings have unique optical signatures, it is possible to ascertain the scan speed of the light beam between any two reference markings. In principle, a minimum of two reference marks are needed to determine the scan speed, one at each of the beginning and end of the scan. However, the calculated speed will generally be different from the actual speed due to variations in the mechanics of the deflecting sub-system 108, such as unevenness in the surface of the mirror, speed variations in the drive-motor, etc. An uneven test surface 102 will also cause variations in scan speed. A more accurate speed determination is obtained by having a number of closely spaced reference markings 12 and computing the scan speed between pairs of markings so that each calculation is made over a shorter span of time.

A calculation of the scan speed between two reference markings 12 is made simply by dividing the distance of travel of the point of intersection of the light beam 107 with the test surface 102 by the elapsed time, namely $V=\Delta s/\Delta t$. As an example, consider the scan taken along a scan line 16 as shown in FIG. 3. The distance of travel ($\Delta s$) is equal to the known separation between a pair of reference markings 12', 12". The elapsed time ($\Delta t$) is determined by taking the difference between the recorded times of detection of the optical signals produced by the impinging light beam upon each of the reference markings 12', 12".

Having obtained the scan speed of the light beam between the two markings, it is now possible to determine the positions of the detected optical signals from the test spots (e.g. 14', FIG. 3) disposed between the two markings 12', 12". As with the reference markings, optical signals resulting from impingement of the light beam upon the test spot 14' will be detected and recorded, along with the times of detection. The position of the test spot 14' relative to the reference marking 12' is computed as the difference between detection times multiplied by the above-computed scan speed.

A more accurate determination of scan speed may be obtained by plotting the known measures of separation between the reference markings versus their times of detection, and applying known curve-fitting techniques to fit the data to a curve, such as a parabola, for example. With this information, it is then a simple matter of interpolating between the measured data points to determine the relative positions of the subsequently detected test spots. This approach avoids making the assumption that the scan speed is linear. By allowing for a more generalized distance-versus-time relationship, the curve-fitting method can provide more precise determinations of position.

It is noted that the spacings between the reference markings 12 need not be equal between every pair of markings. Certain of the reference markings may be more closely spaced than others in order to achieve higher precision in the determination of the scan speed. This may be needed, for example, if it is known that the deflecting sub-system 108 moved the beam faster at certain places on the plate 10. For example, the scan speed of the beam may be faster at the central portion of the test surface than at the periphery. Similarly, in the case where the test surface 102 is nonplanar, the scan speed will vary due to the uneven surface. In general, by varying the spacing of the reference markings on the plate, it is possible to account for changes in the variations of the scan speed of the beam as the beam is scanned across the surface of the plate, thus assuring additional precision in the subsequent determination of position.

Having the reference markings on the same plate as the test spots offers advantages over using a separate reference plate to calibrate the speed of the scanning optics. First, there is no need to perform a calibration step for the scan speed. The approach used in the present invention effectively provides for a continuous self-calibration, since the reference markings are already present on the plate surface along with the test spots. Typically, calibration of the scanning optics must be performed periodically, and so much time can be saved by the approach of the present invention. Second, since the reference markings and the test spots are on the same surface, proper registration is maintained. There is no possibility of an offset or other misalignment as there would be if a separate calibration plate is used. The positions of the test spots on the surface are accurately computed relative to the reference markings which are on the same surface.

Figure 6:
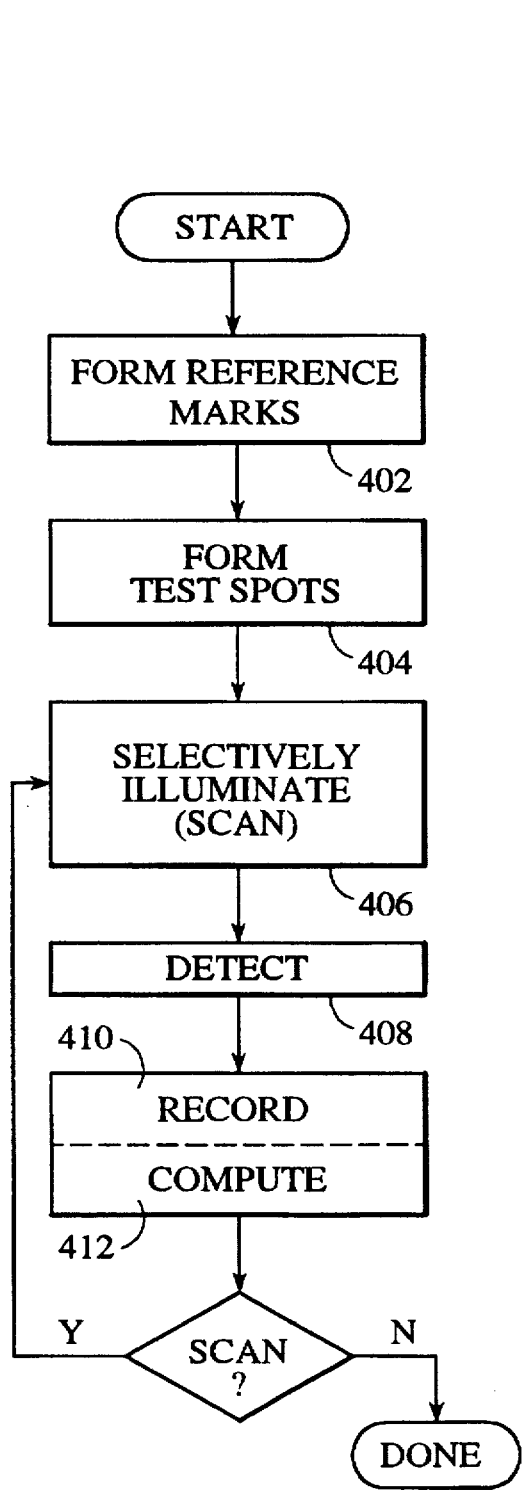
FIGS. 6 and 7 are flow charts showing generally the steps of the method of making optical measurements according to the present invention.
Figure 7:
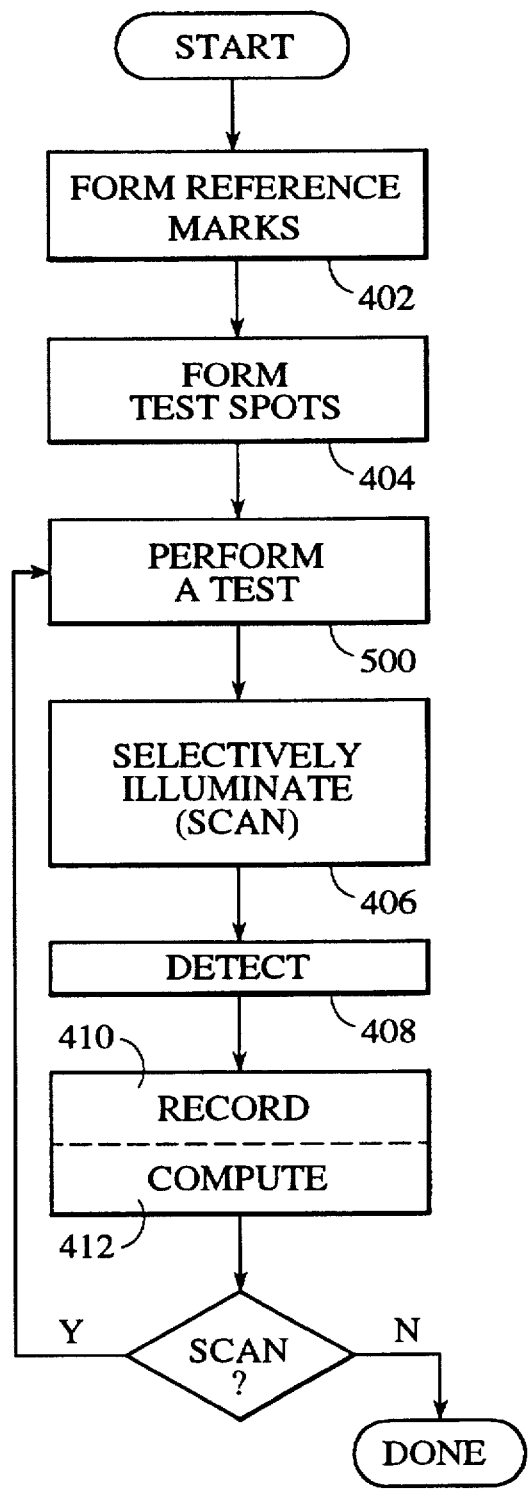

Turning now to FIGS. 6 and 7, the steps in making optical measurements in accordance with the present invention are summarized. FIG. 6 shows the basic steps, beginning with forming reference markings 402 on the surface of a plate and disposing the chemical and biological materials 404 in selected areas of the surface. Next, a light beam is directed onto the surface and scanned to selectively illuminate 406 each of the reference markings and chemical and biological materials. The resulting optical signals are then detected 408 by a detector and recorded 410 on a storage medium along with the time of the detection. The scanning 406, detecting 408 and recording 410 steps are continued until the surface has been "fully" scanned. This may involve the accumulation of data over two or more scan cycles wherein the entire surface is scanned and data is collected for each scan cycle. FIG. 6 shows that the step of recording 410 may further include a step of computing the positions 412 of the detected optical signals. Alternatively, the computation step 412 may be performed after the surface is fully scanned and all of the optical data has been collected and recorded.

FIG. 7 shows a variation wherein a test can be performed 500 on the chemical and biological materials prior to the step of selective illumination 406. More generally, each scan cycle may be preceded by performing a test on the materials, as shown in FIG. 7. This provides flexibility in that the course of an experiment on the materials can be performed and controlled based upon the results of previous tests 500. For example, after a scan, the plate may be removed from the optical measurement system, subjected to certain chemical treatments and then rescanned by the system.

Figure 4:
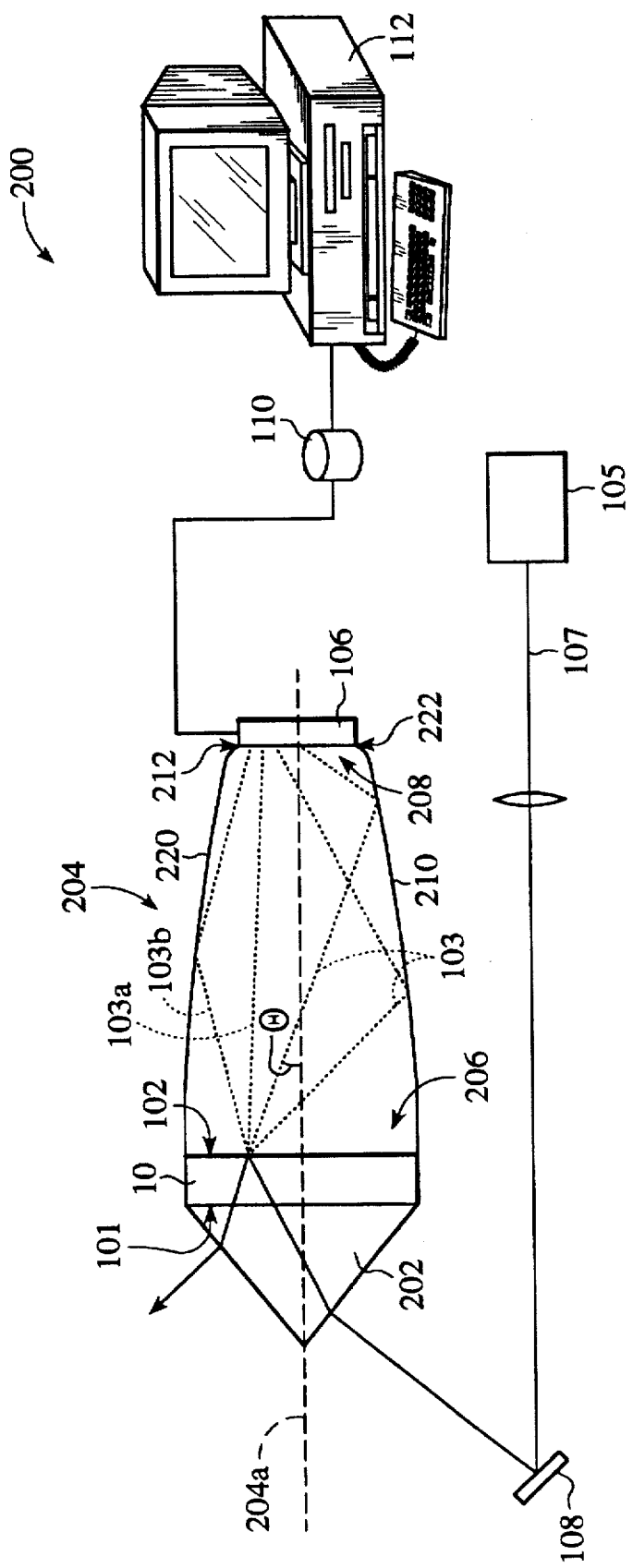
FIG. 4 illustrates an optical measurement system of the present invention which employs a Winston concentrator.

The discussion will now turn to particular embodiments of the present invention beginning with the arrangement shown in FIG. 4. The elements of the optical detection system 200 in FIG. 4 which are common to those illustrated in FIG. 1 are represented by the same reference numerals. The system 200 shown in FIG. 4 employs an arrangement of light collection optics known as a Winston concentrator 204, or more generically a compound parabolic concentrator. The concentrator 204 is composed of two parabolic mirrors 210, 220 symmetrically arranged about an axis 204a of the concentrator 204. An entry aperture 206 is defined by the symmetrically arranged mirrors at an end opposite the vertices of the parabolic mirrors 210, 220. An exit aperture 208 is defined by the foci of the parabolic mirrors. Thus, the focus 212 of the parabola which defines the shape of the first mirror 210 and the focus 222 of the parabola which defines the shape of the second mirror 220 together determine the location and size of the exit aperture 208. The Winston concentrator 204 has the property that light entering through the entry aperture 206 at an angle no greater than a maximum angle θ relative to the concentrator axis 204a will exit through the exit aperture 208, either by a direct light path 103a or by a reflected light path 103b. A comprehensive treatment of the underlying principles of compound parabolic mirrors, and nonimaging optics in general, is provided in the reference entitled "High Collection Nonimaging Optics," by W. T. Welford and R. Winston, Academic Press, Inc., 1989.

In the embodiment shown in FIG. 4, the plate 10 is a transparent substrate. The plate 10 is received in the entry aperture 206 such that a front face of the plate faces the interior region of the concentrator 204, toward the exit aperture 208, and serves as the test surface 102. The rear face 101 of the plate 10 is coupled to a prism 202. The detector 106 is aligned with the exit aperture 208 and provides a measurement of the total amount of light impinging the detector at any given time. The output of the detector 106 is recorded on the storage medium 110, as is the time at which the measurement is taken.

A light beam 107, generated by the light source 105, is directed by the deflecting sub-system 108 onto an exposed face of the prism 202. Due to a difference between refractive indices of the prism 202 and the atmosphere, the light beam 107 is bent toward the rear face 101 of the transparent plate 10. The light beam continues through the thickness of the plate toward the test surface 102, striking the test spots 14 (FIG. 2) and reference markings 12 formed on the test surface as the light beam is raster scanned across the test surface. The individual occurrences of optical signals arising from the impinging light beam are detected by the detector 106.

For example, FIG. 4 shows the light beam 107 striking a region of the test surface 102. The light 103 from the optical signals produced by the object (either a test spot or a reference marking) is directed by the parabolic mirrors 210, 220 of the concentrator 204 toward the detector 106, the output of which is recorded as described above. This process is repeated as the light beam is made to scan the area of the test surface 102.

It is important that the light beam 107 itself is not detected by the detector 106. The measured optical data would be masked if the data included the effects of the light beam. This situation is avoided by preventing the light beam from entering the concentrator 204. To achieve this, the incident angle of the light beam within the transparent plate 10 relative to the test surface 102 is chosen to be greater than the so-called critical angle so that there is total internal reflection of the light beam 107. With total internal reflection, the light beam will not enter the interior region of the concentrator 204 and so will not affect the measurements of the detected optical signals.

In one type of Winston concentrator 204 (not shown), the parabolic surfaces of the two mirrors 210, 220 are rotated about the axis 204a of the concentrator. This forms a surface of rotation which encloses a volume of space, the interior of which provides a very efficient transmission of light from the test surface 102 to the detector 106.

Figure 5:
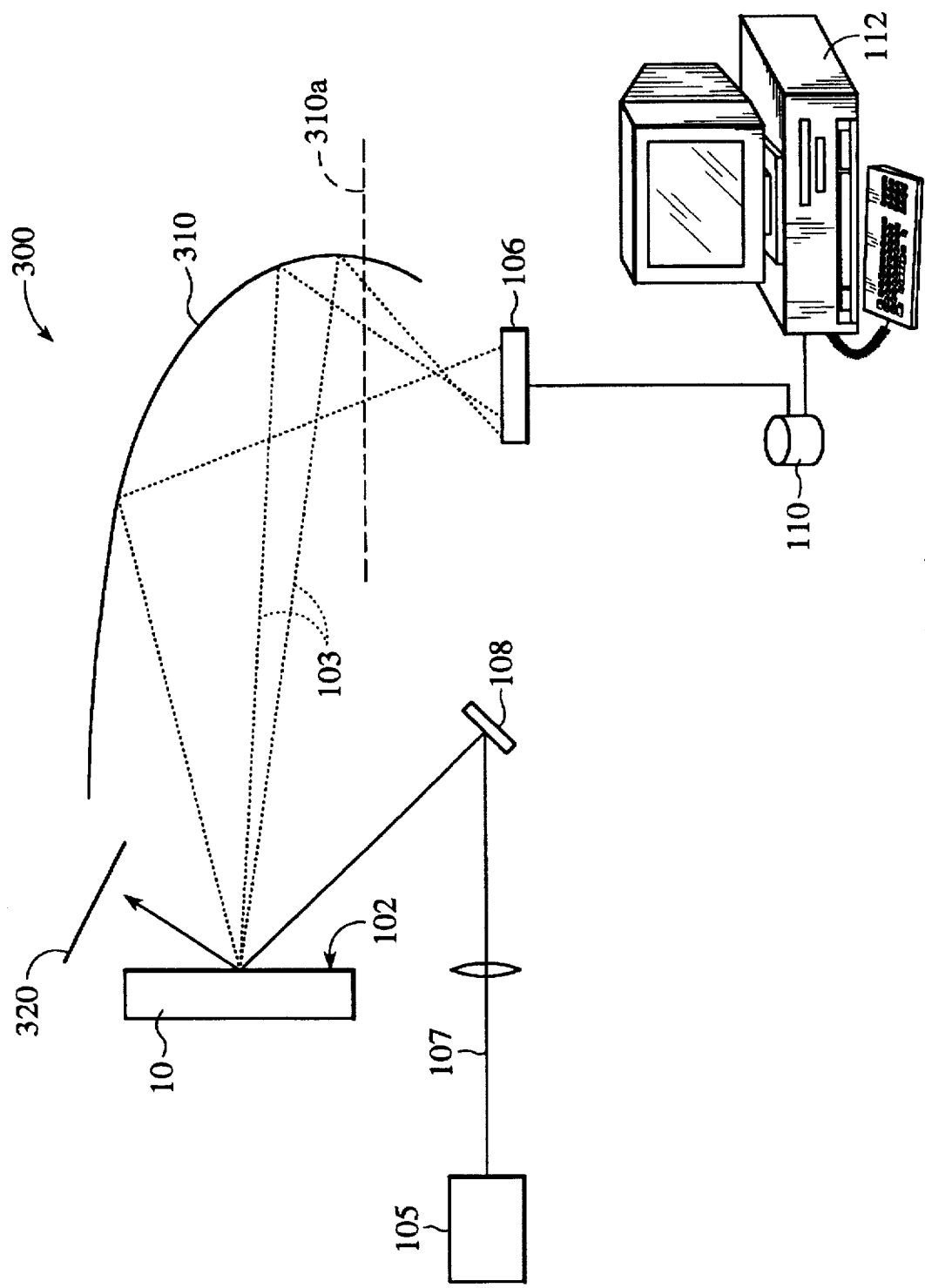
FIG. 5 illustrates an optical measurement system of the present invention which employs an off-axis parabolic mirror.

Turning now to FIG. 5, another embodiment of the present invention will be described. In the optical detection system 300 shown in FIG. 5, an off-axis parabolic mirror arrangement is employed. Elements shown in FIG. 1 which also occur in FIG. 5 are identified by the same reference numerals. The light beam 107 is directed onto the test surface 102 and scanned across the surface as described above. A parabolic mirror 310 is used to direct light emissions 103 from the test surface 102 to the detector 106, for recording on the storage medium 110. As can be seen, the plate 10 is positioned out of alignment relative to the axis 310a of the parabola which defines the shape of the mirror 310. The detector 106 is placed in close proximity to the focus of the parabola which defines the mirror. Alternatively, the detector can be displaced away from the focus if additional optics (not shown) are located at the focus so as to direct the light arriving at the focus to the detector. In a variation of the embodiment shown in FIG. 5, the parabolic mirror can surround most of the test surface by rotating the reflective surface of the mirror. A small cutaway section must be provided to allow access of the light beam 107.

Since there is reflection of the light beam 107 from the test surface 102, it may be necessary to block such reflections so that they are not subsequently directed by the mirror 310 to the detector 106, thereby preventing detection of the desired optical activity of the test spots 14 (FIG. 2) and reference markings 12. The blocking of such reflected light is accomplished by the use of a light barrier 320, which prevents light that is reflected off the test surface 102 from being directed to the detector 106.

For example, where the optical signals of interest are small in comparison to the reflected light, the weaker signals would be masked by the stronger incident light and so a light barrier 320 would be appropriate. On the other hand, if the reflected light is discernible from the signals of interest, a light barrier would not be required. For instance, the reflected light may have a wavelength different from those of the signals of interest, allowing for the use of filters to filter out the reflected light.

I claim:

1. A method of measuring optical properties of optically detectable substances, including the steps of:

provuding a surface;

forming reference marks on said surface, including selecting areas on said surface and interspersing said reference marks among said selected areas, said step of forming reference marks further including selecting known spacings therebetween;

forming a plurality of test spots by disposing said optically detectable substances upon said selected areas;

selectively illuminating portions of said surface with light, forming a light spot thereon, said light spot illuminating at least some of said test spots and said reference marks;

detecting an optical property of each of a plurality of said test spots and said reference marks, including for each detection the substeps of recording said optical property and recording the time of said detection; and computing positions of said test spots on said surface based upon said recorded times of detection.

2. The method of claim 1 further including a step of performing a test on some of said test spots, said step of performing a test being taken prior to said step of selectively illuminating portions of said surface.

3. The method of claim 2 further including repeating said steps of performing a test, selectively illuminating portions of said surface, and detecting an optical property.

4. The method of claim 1 wherein said step of forming reference marks further includes selecting varying spacings between said reference marks.

5. The method of claim 1 wherein said step of computing positions of said test spots includes substeps of:

plotting data points representing relative positions of said reference marks versus recorded times of detection of said reference marks;

fitting a curve to said data points; and interpolating between said data points for said recorded times of detection of said test spots, basing said interpolating on said curve.

6. The method of claim 1 wherein said step of computing positions of said test spots includes substeps of:

computing a rate of motion of said light spot between two of said reference marks, including dividing a measure of spacing between said two reference marks by the difference between said recorded times of detection of said two reference marks;

computing a time difference between said recorded time of detection of one test spot positioned between said two reference marks and said recorded time of detection of a first of said two reference marks; and multiplying said rate of motion of said light spot by said time difference, thereby determining a position of said one test spot relative to said first of said two reference marks.

7. An optical detection system for detecting a plurality of optically tagged biological and chemical materials, including:

a source of collimated light;

a surface onto which said optically tagged biological and chemical materials are disposed;

a plurality of reference marks disposed on said surface, said reference marks being spaced apart by known amounts, said reference marks being optically distinguishable from said optically tagged biological and chemical materials;

raster means for directing said collimated light across said surface in raster fashion so that said collimated light impinges upon said optically tagged biological and chemical materials and said reference marks, wherein impingement by said collimated light gives rise to optical signals;

means for detecting said optical signals, including means for storing a parameter of said optical signals and means for storing the time of each detection of said optical signals; and computing means, in communication with said means for storing the time of detection, for determining positions of said optically tagged biological and chemical materials.

8. The optical detection system of claim 7 wherein said optical signals result in the transmission of electromagnetic (EM) energy from said surface, the optical detection system further including collector means for directing said transmission of EM energy to said means for detecting.

9. The optical detection system of claim 8 wherein said collector means is a portion of a parabolic mirror arranged between said surface and said means for detecting such that light emissions of said optical signals from said surface are directed to said means for detecting.

10. The optical detection system of claim 8 wherein said collector means is a compound parabolic concentrator having two parabolic mirrors symmetrically arranged about an axis, said means for detecting being positioned proximate to and in alignment with foci of said two parabolic mirrors, said surface being positioned opposite to and facing said means for detecting so that light emissions of said optical signals from said surface are reflected by said two parabolic mirrors toward said means for detecting.

11. The optical detection system of claim 10 wherein said two parabolic mirrors are curved about said axis to form a parabolic surface of rotation about said axis.

12. The optical detection system of claim 7 wherein said surface is a front face of a transparent substrate, said collimated light being directed by said raster means upon a rear face of said transparent substrate, wherein said collimated light impinges upon said optically tagged biological and chemical materials and said reference marks by traversing through a thickness of said transparent substrate toward said front face.

13. The optical detection system of claim 7 wherein a first pair of said reference marks is spaced apart by a first measure of separation and a second pair of said reference marks is spaced apart by a second measure of separation.

14. The optical detection system of claim 7 wherein reference marks disposed on a central portion of said surface are more closely spaced than reference marks disposed on a periphery of said surface.

15. The optical detection system of claim 7 wherein said reference marks have optical signatures unique thereto so as to be distinguishable from optical signatures of said optically tagged biological and chemical materials.

16. The optical detection system of claim 7 wherein said means for detecting includes a first detector for detecting optical signals originating from said optically tagged biological and chemical materials, and a second detector for detecting optical signals originating from said reference marks.

17. An optical detection system for measuring optical tags attached to selected molecules in chemical and biological specimens, including:

a laser beam source for generating a beam of light;

means for deflecting said beam of light;

an optically transparent plate having a front surface onto which said chemical and biological specimens are disposed, said transparent plate having a rear surface opposite said front surface, said front surface having optically identifiable reference marks formed thereon, said reference marks having known measures of separation therebetween;

electromagnetic energy (EM) detection means for generating output signals in response to detection of electromagnetic energy;

a parabolic concentrator having a central axis and further having at least two parabolic reflective surfaces symmetrically arranged about said central axis, said at least two parabolic reflective surfaces defining an entry aperture formed at a first end of said concentrator and further defining an exit aperture formed at an end opposite said first end, foci of said two parabolic reflective surfaces being proximate said exit aperture; and computation means for computing positions of said chemical and biological specimens disposed upon said front surface, including memory means for storing said output signals generated by said EM detection means and for storing a time value indicating the time at which said EM detection means generates said output;

said optically transparent plate being received in said entry aperture of said concentrator such that said front surface is directed toward said exit aperture;

said EM detection means being received in said exit aperture of said concentrator;

said beam of light being scanned across said rear surface of said optically transparent plate by said means for deflecting, said beam of light passing through said optically transparent plate to impinge upon said chemical and biological specimens and said reference marks;

wherein impingement of said beam of light results in electromagnetic energy emissions from each of said chemical and biological specimens and said reference marks, said emissions being directed by said concentrator to said EM detection means, thereby generating output signals from said EM detection means.

18. The optical detection system of claim 17 wherein said at least two parabolic reflective surfaces are curved about said axis of said concentrator to form a parabolic surface of rotation about said axis.

19. The optical detection system of claim 17 further including a prism coupled to said rear surface so that said means for deflecting directs said beam of light upon a surface of said prism, said beam of light passing through said prism and across a prism-rear surface interface with minimum refraction.

20. The optical detection system of claim 17 wherein said front surface of said transparent plate is non-planar.

21. The optical detection system of claim 17 wherein at least two of said measures of separation between said reference marks are unequal.

* * * * *